(12) United States Patent
Venturelli

(10) Patent No.: US 7,264,619 B2
(45) Date of Patent: Sep. 4, 2007

(54) CATHETER WITH FLEXIBLE COOLED ELECTRODE

(75) Inventor: Andrea Venturelli, Concesio (IT)

(73) Assignee: Fogazzi di Venturelli Andrea & C. S.n.c., Concesio (Brescia) (IT)

( * ) Notice: Subject to any disclaimer, the term of this patent is extended or adjusted under 35 U.S.C. 154(b) by 417 days.

(21) Appl. No.: 10/943,869

(22) Filed: Sep. 20, 2004

(65) Prior Publication Data

US 2005/0090880 A1  Apr. 28, 2005

Related U.S. Application Data

(63) Continuation of application No. PCT/IT03/00027, filed on Jan. 27, 2003.

(30) Foreign Application Priority Data

Mar. 20, 2002  (IT)  .................. BS20020039 U

(51) Int. Cl.
*A61B 18/14* (2006.01)
(52) U.S. Cl. ...................................... 606/41
(58) Field of Classification Search .................. 606/41
See application file for complete search history.

(56) References Cited

U.S. PATENT DOCUMENTS

| 4,945,912 | A | * | 8/1990 | Langberg ................. 600/374 |
| 4,976,711 | A | * | 12/1990 | Parins et al. ............... 606/48 |
| 5,242,451 | A | * | 9/1993 | Harada et al. ............ 623/1.18 |
| 5,281,217 | A | * | 1/1994 | Edwards et al. ............. 606/41 |
| 5,555,618 | A | * | 9/1996 | Winkler ..................... 29/825 |
| 5,562,641 | A | * | 10/1996 | Flomenblit et al. ........ 604/531 |
| 5,573,509 | A | * | 11/1996 | Thornton ............... 604/102.02 |
| 5,603,697 | A | * | 2/1997 | Grundy et al. ........... 604/95.04 |
| 5,647,871 | A | * | 7/1997 | Levine et al. ................ 606/45 |
| 5,665,103 | A | * | 9/1997 | Lafontaine et al. ......... 606/192 |
| 5,735,847 | A | * | 4/1998 | Gough et al. ................ 606/41 |
| 5,741,249 | A | * | 4/1998 | Moss et al. .................. 606/33 |
| 5,755,760 | A | * | 5/1998 | Maguire et al. ............ 607/122 |
| 5,800,482 | A | * | 9/1998 | Pomeranz et al. .......... 607/101 |
| 5,860,974 | A | * | 1/1999 | Abele ......................... 606/41 |
| 5,913,854 | A | * | 6/1999 | Maguire et al. .............. 606/41 |
| 5,951,546 | A | * | 9/1999 | Lorentzen .................... 606/41 |
| 6,002,956 | A | * | 12/1999 | Schaer ...................... 600/381 |
| 6,071,279 | A | * | 6/2000 | Whayne et al. .............. 606/41 |
| 6,090,104 | A | * | 7/2000 | Webster, Jr. ................. 606/41 |
| 6,119,041 | A | * | 9/2000 | Pomeranz et al. .......... 607/101 |
| 6,258,118 | B1 | * | 7/2001 | Baum et al. ................ 623/1.19 |
| 6,265,691 | B1 | * | 7/2001 | Cardineau et al. ..... 219/121.69 |
| 6,280,441 | B1 | * | 8/2001 | Ryan .......................... 606/45 |
| 6,314,962 | B1 | * | 11/2001 | Vaska et al. ................ 128/898 |
| 6,315,778 | B1 | * | 11/2001 | Gambale et al. ............. 606/41 |
| 6,322,559 | B1 | * | 11/2001 | Daulton et al. .............. 606/41 |
| 6,348,067 | B1 | * | 2/2002 | Baum et al. ............... 623/1.19 |

(Continued)

*Primary Examiner*—Michael Peffley
*Assistant Examiner*—Alex Toy
(74) *Attorney, Agent, or Firm*—Shoemaker and Mattare

(57) ABSTRACT

A catheter for the treatment of tumors and other affections using hyperthermia induced by radio frequency includes a tubular body with or without an anchoring balloon at its distal end. An active electrode is positioned around the body and connected to a radio frequency generator. At least one thermistor needle measures the temperature around the electrode. The active electrode is flexible and connectable to a supply source of a fluid for cooling the electrode. It includes a helical conduit, which can be metal, conductive ceramic or graphite.

10 Claims, 2 Drawing Sheets

U.S. PATENT DOCUMENTS

| | | | |
|---|---|---|---|
| 6,356,790 B1 * | 3/2002 | Maguire et al. | 607/102 |
| 6,358,245 B1 * | 3/2002 | Edwards et al. | 606/34 |
| 6,458,123 B1 * | 10/2002 | Brucker et al. | 606/41 |
| 6,461,351 B1 | 10/2002 | Woodruff et al. | |
| 6,471,697 B1 * | 10/2002 | Lesh | 606/41 |
| 6,500,174 B1 * | 12/2002 | Maguire et al. | 606/41 |
| 6,579,288 B1 * | 6/2003 | Swanson et al. | 606/41 |
| 6,607,502 B1 * | 8/2003 | Maguire et al. | 604/22 |
| 6,669,692 B1 * | 12/2003 | Nelson et al. | 606/41 |
| 6,758,847 B2 * | 7/2004 | Maguire | 606/41 |
| 6,771,996 B2 * | 8/2004 | Bowe et al. | 600/374 |
| 6,986,769 B2 * | 1/2006 | Nelson et al. | 606/41 |
| 2001/0011161 A1 | 8/2001 | Edwards et al. | |
| 2002/0198519 A1 * | 12/2002 | Qin et al. | 606/34 |
| 2003/0065317 A1 * | 4/2003 | Rudie et al. | 606/33 |
| 2003/0236518 A1 * | 12/2003 | Marchitto et al. | 606/27 |
| 2004/0024402 A1 * | 2/2004 | Nita | 606/45 |

* cited by examiner

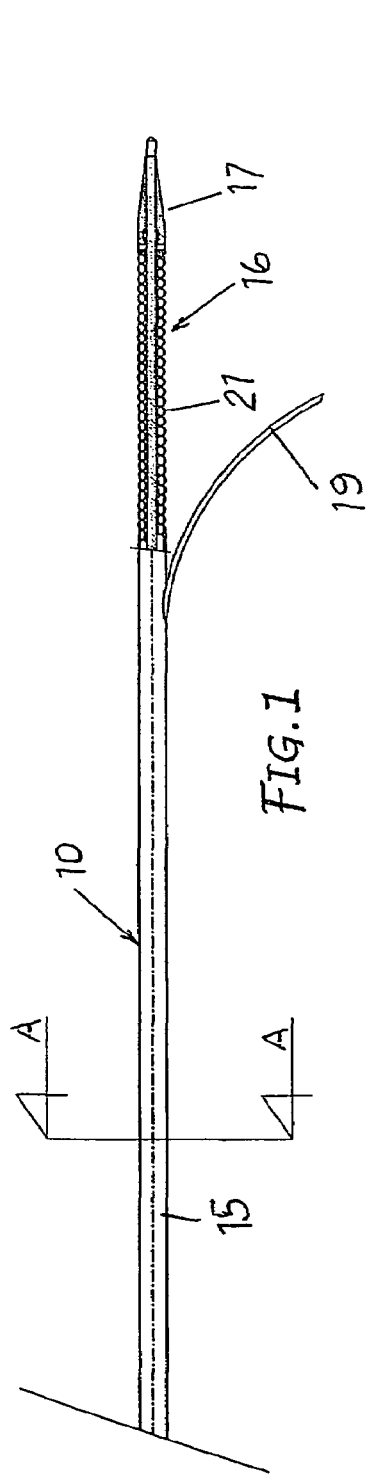
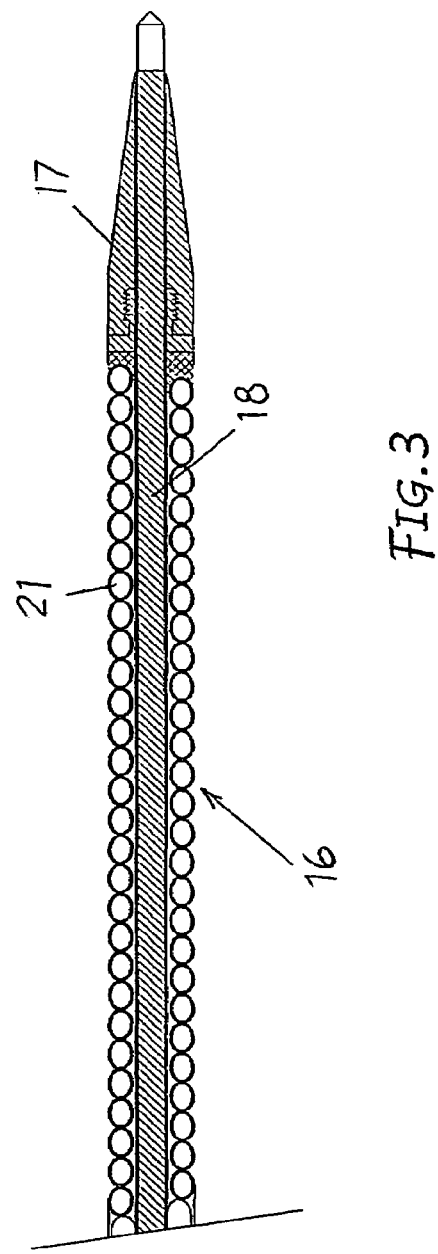
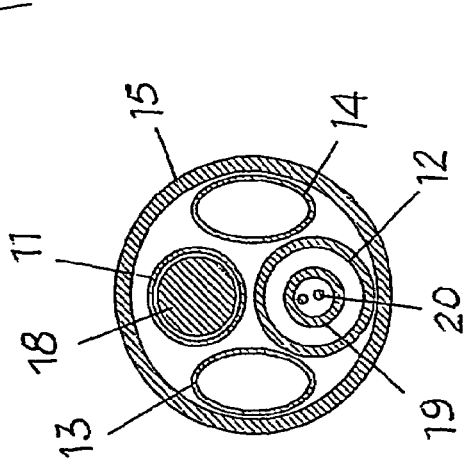
FIG. 1
FIG. 3
FIG. 2

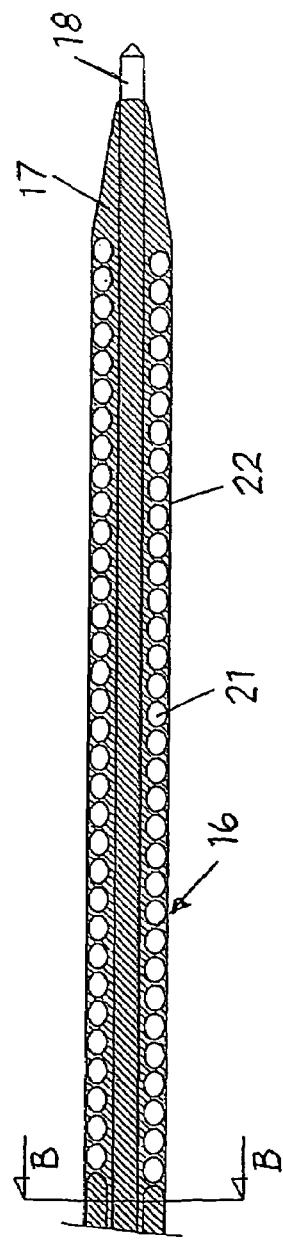
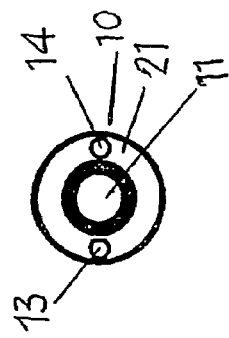
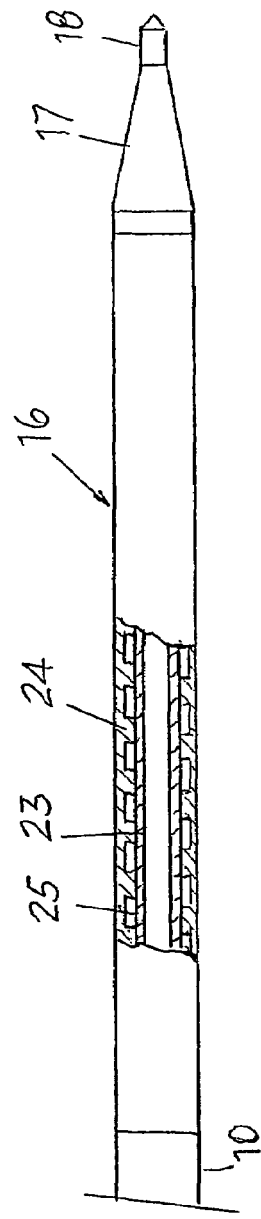
FIG. 4
FIG. 5
FIG. 6

CATHETER WITH FLEXIBLE COOLED ELECTRODE

REFERENCE TO EARLIER APPLICATION

This Application is a continuation of International Application No. PCT/IT03/00027, filed Jan. 27, 2003, by A. Venturelli, entitled Catheter With Flexible Cooled Electrode, which claims the benefit of Italian Patent Application No. BS2002U000039, filed Mar. 20. 2002.

BACKGROUND OF THE INVENTION

1. Field of the Invention

This invention concerns in general devices for therapeutic and surgical use in the treatment of tumors and other affections using hyperthermia, that is thermal ablation, induced by radio frequency, and refers in particular to a catheter with an electrode for this use.

2. Description of Related Art

There already are some well known catheters for the purpose mentioned, among which is one using a metal plaque as an active electrode, connectable to a radio frequency generator, positioned along a tubular body of the catheter near the distal metal point and/or a possible inflatable anchoring balloon. The plaque can be copper, steel or some other metal. It partially encompasses at least the tubular body of the catheter and, to avoid exceeding the treatment temperature induced by the radio frequency, which could cause burns, must be cooled.

For this purpose, the plaque has a double wall to form a cavity or hollow space in which a cooling fluid is circulated, usually water, supplied by an appropriate source. However, an active electrode in the form of a plaque designed in this way forms a rigid section, which has a negative influence on the flexibility of the catheter where it is housed, and, above all, is not easy to manufacture.

SUMMARY OF THE INVENTION

One of the objects of this invention is to propose a catheter for local treatments using hyperthermia induced by radio frequency equipped with an active electrode having a new configuration that is advantageously flexible.

Another object of the invention is to provide a cooled electrode which integrates well with the smoothness and flexibility characteristics of the body of the catheter and which is easier to manufacture and decidedly efficient.

These objects are achieved in a catheter for therapeutic and surgical treatment using radio frequency having a distal part, which houses an electrode made up of a helical duct, coaxial with the catheter tube, attached to a metal point and/or a possible anchoring balloon, and is connectable to a radio frequency generator and a supply source of cooling fluid.

The duct containing the electrode can be made in different ways, with different shapes and with various conductive materials, and results in being advantageously flexible, facilitating the introduction and use of the catheter in the affected part to be treated as required.

BRIEF DESCRIPTION OF THE DRAWINGS

Greater details of the invention will become more evident in the following description made with reference to the following illustrative and non-limiting drawings, in which:

FIG. 1 is a partial cross-sectional detail view of a portion of a catheter including an active electrode constructed according to principles of the invention;

FIG. 2 is an enlarged cross-sectional detail view drawn along line A-A in FIG. 1;

FIG. 3 is an enlarged cross-sectional detail view of an embodiment of an electrode constructed according to principles of the invention;

FIG. 4 is an enlarged cross-sectional detail view of an embodiment of another electrode constructed according to principles of the invention;

FIG. 5 is a cross-sectional detail view drawn along line B-B in FIG. 4; and

FIG. 6 an enlarged cross-sectional detail view of an embodiment of a further electrode constructed according to principles of the invention.

DETAILED DESCRIPTION OF THE PREFERRED EMBODIMENTS

As represented, the catheter includes a body 10, which can be made up of a tubular element with a number of ducts or, as shown, with several tubes 11, 12, 13 and 14 located side by side longitudinally and enclosed in an insulating elastic sheath 15. In its distal part, the body of the catheter houses an active electrode 16, which will be described below, plus a metal point end piece 17 with or without an anchoring balloon (not shown). In a proximal part (not shown), the catheter is equipped with connectors for connection to the control devices of the various functions provided.

Between the ducts or tubes in the body 10 of the catheter, one duct or tube 11 is allocated for receiving a guide wire or spindle 18, which can extend as far as the metal point. The metal point 17 and possible balloon are attached to the free end of the tube 11, and the electrode 16 is positioned directly or indirectly around a portion of the tube.

Another duct or tube 12 is allocated to receive a thermistor needle 19, which extends until it protrudes, in a retractable form, from one side of the body 10 near the electrode 16. The needle 19 is usually tubular and may have an external coating. The leads 20 of a thermocouple for measuring the temperature around the electrode pass through the needle.

Other ducts or tubes 13 and 14 are envisaged for the delivery and return of a cooling fluid, preferably water, to the electrode 16, leading from a cooling liquid supplier.

The active electrode 16 is made up of a helical duct 21. It is coaxial with the catheter body, that is, around the tube 11, or a tubular element attached to the latter, and connects with an appropriate radio frequency generator by means of a lead (not shown) passing through the body of the catheter.

Duct 21 can be metal, conductive ceramic, graphite or other suitable material, and the cross section thereof may be of any shape, round, oval, rectangular, etc. The duct 21 can be constructed in several ways. For example, it can be formed into a single helical shape, achieved by turning a single tubular initial element helicoidally in an intermediate part. Portions from opposite parts of the helicoidal zone represent, all or in part, fluid delivery and return tubes 13, 14, which must flow along and cool the electrode 16.

According to another embodiment, the duct 21 housing the electrode 16 can be double helical, achieved by winding parts of the two parallel branches of an initial tubular element, already bent into a U shape, contemporarily and helically, so that two straight sections of said branches of the initial tubular element enclose, all or in part, fluid delivery and return tubes 13,14 which cool the electrode.

The coils of the electrode in the shape of a helical duct 21 can be linked together, centrally to tube 11 or the tubular element around which they are wound, by a resin or an adhesive. Externally, they may be free, as shown in FIG. 3. Preferably, they may be enclosed in a sheath 22, as shown in FIG. 4, which can either be a conductive ceramic or graphite. However, the electrode remains suitably flexible.

When electrode 16 is used in a conductive ceramic or graphite covering, the helical duct 21 can be enclosed in two cylindrical, concentric and attached sleeves, one internal 23 and the other external 24, as shown in FIG. 6. In this way, at least in the surface of one sleeve in contact with the other sleeve, there is at least one helical duct 25 to form the helical passage required. This helical passage has, preferably and advantageously, a rectangular cross section. The delivery and return tubes 13,14 for the electrode cooling fluid are intended to be connected to it.

The invention is not limited to the particular embodiments described herein, rather only to the following claims.

I claim:

1. A catheter for the treatment of tumors and other affections using hyperthermia induced by radio frequency comprising:
    a tubular body equipped with a metal point at a distal end thereof;
    an active electrode placed around said body, attached to said metal point, and connected to a radio frequency generator; and
    at least one thermistor needle to measure a temperature around said electrode;
    wherein said active electrode is flexible and connectable to a cooling fluid supply source for cooling said electrode, wherein
    said electrode is formed of two concentric and attached cylindrical sleeves, wherein a surface of one of said sleeves is helically grooved and forms with a surface of another of said sleeves at least one helical passage connectable to two tubes for delivery and return of the electrode cooling fluid.

2. The catheter according to claim 1, wherein said flexible electrode includes a helical duct coaxial and attached to a section of said tubular body of said catheter.

3. The catheter according to claim 1, wherein said flexible electrode defines a single helical tube and is connected to a radio frequency generator.

4. The catheter according to claim 1, wherein:
    said flexible electrode is formed of a helically wound tubular element; and
    opposite ends of said tubular element are connected to or merge into two tubes for delivery and return of the electrode cooling fluid.

5. The catheter according to claim 1, wherein said flexible electrode defines a double helical tube and is connected to a radio frequency generator.

6. The catheter according to claim 1, wherein:
    said flexible electrode comprise two parallel sections of a helically wound tubular element;
    said sections comprise two branches of a tubular element bent so as to become joined; and
    free ends of each coil are connected to or part of two tubes for delivery and return of the electrode cooling fluid.

7. The catheter according to claim 4, wherein said helically wound tubular element is constructed of metal, conductive ceramic, or graphite.

8. The catheter according to claim 1, wherein said electrode is attached to said body by a resin seal or adhesive.

9. The catheter according to claim 1, wherein said electrode is enclosed externally in a sheath or sleeve constructed of ceramicor graphite.

10. The catheter according to claim 1, wherein: said sleeves are constructed of conductive ceramic or graphite.

* * * * *